(12) United States Patent
Niklasson

(10) Patent No.: US 7,798,976 B2
(45) Date of Patent: Sep. 21, 2010

(54) EPICUTANEOUS TEST PLASTER

(75) Inventor: Bo Johan Niklas Niklasson, Malmö (SE)

(73) Assignee: Chemotechnique MB Diagnostics AB, Tygelsjo (SE)

( * ) Notice: Subject to any disclaimer, the term of this patent is extended or adjusted under 35 U.S.C. 154(b) by 65 days.

(21) Appl. No.: 10/501,555

(22) PCT Filed: Jan. 16, 2003

(86) PCT No.: PCT/SE03/00059

§ 371 (c)(1),
(2), (4) Date: Jul. 16, 2004

(87) PCT Pub. No.: WO03/059171

PCT Pub. Date: Jul. 24, 2003

(65) Prior Publication Data

US 2005/0043648 A1    Feb. 24, 2005

(30) Foreign Application Priority Data

Jan. 16, 2002    (SE) .................................. 0200102

(51) Int. Cl.
- A61B 5/00 (2006.01)
- A61B 17/06 (2006.01)
- A61B 19/02 (2006.01)
- A61B 17/20 (2006.01)
- A61L 15/00 (2006.01)
- A61M 37/00 (2006.01)

(52) U.S. Cl. .................. 600/556; 206/438; 604/46; 604/47

(58) Field of Classification Search ................ 600/556, 600/306; 604/46–47; 206/438, 440, 538
See application file for complete search history.

(56) References Cited

U.S. PATENT DOCUMENTS

| | | | | |
|---|---|---|---|---|
| 3,894,531 | A * | 7/1975 | Saunders, Jr. ................ | 600/556 |
| 4,158,359 | A * | 6/1979 | Kurokawa et al. .......... | 600/300 |
| 4,450,844 | A * | 5/1984 | Quisno ......................... | 600/556 |
| 4,450,845 | A * | 5/1984 | Engel ........................... | 600/556 |
| 4,472,507 | A * | 9/1984 | Pluim, Jr. .................... | 436/131 |
| 4,543,964 | A * | 10/1985 | Breneman ................... | 600/556 |

(Continued)

FOREIGN PATENT DOCUMENTS

DE    3811564 A1 * 10/1989

(Continued)

*Primary Examiner*—Max Hindenburg
*Assistant Examiner*—Adam J. Eiseman
(74) *Attorney, Agent, or Firm*—Capitol City TechLaw

(57) ABSTRACT

An epicutaneous test plaster, which is intended for removable adhesion to a skin portion of a person subjected to testing, has a flexible carrier (10) with a medical adhesive layer (12) and a number of test chambers (31). The test chambers contain a filter element (17) for absorption of allergen and are oriented with their opening directed away from the flexible carrier (10). A removable cover layer (27, 32) extends over all the test chambers and the carrier (10) and is removably secured to them by means of the adhesive layer (12) of the carrier. According to the invention, the test chambers (31) are formed as separate chambers, which are each separately fixed to the carrier and which are made up of a number of different sub-layers (13, 17, 19, 20, 24, 26).

20 Claims, 3 Drawing Sheets

U.S. PATENT DOCUMENTS

| | | | |
|---|---|---|---|
| 4,765,986 A | * | 8/1988 | Liedtke ........................ 424/449 |
| 4,809,707 A | * | 3/1989 | Kraft et al. ................... 600/549 |
| 4,887,611 A | * | 12/1989 | Rudiger et al. .............. 600/556 |
| 5,044,372 A | | 9/1991 | Anhauser et al. |
| 5,325,864 A | | 7/1994 | Gerber |
| 5,874,226 A | * | 2/1999 | Zeytinoglu et al. ............ 435/7.1 |
| 5,944,662 A | * | 8/1999 | Schoendorfer ............... 600/362 |
| 6,142,954 A | * | 11/2000 | Anhauser et al. ............. 600/556 |
| 6,143,945 A | * | 11/2000 | Augustine et al. ............. 602/41 |
| RE37,934 E | * | 12/2002 | Hoffmann ................... 424/449 |

FOREIGN PATENT DOCUMENTS

| | | |
|---|---|---|
| NL | 8701577 | 2/1989 |
| WO | WO 94/17735 | 8/1994 |
| WO | WO 99/08601 | 2/1999 |

* cited by examiner

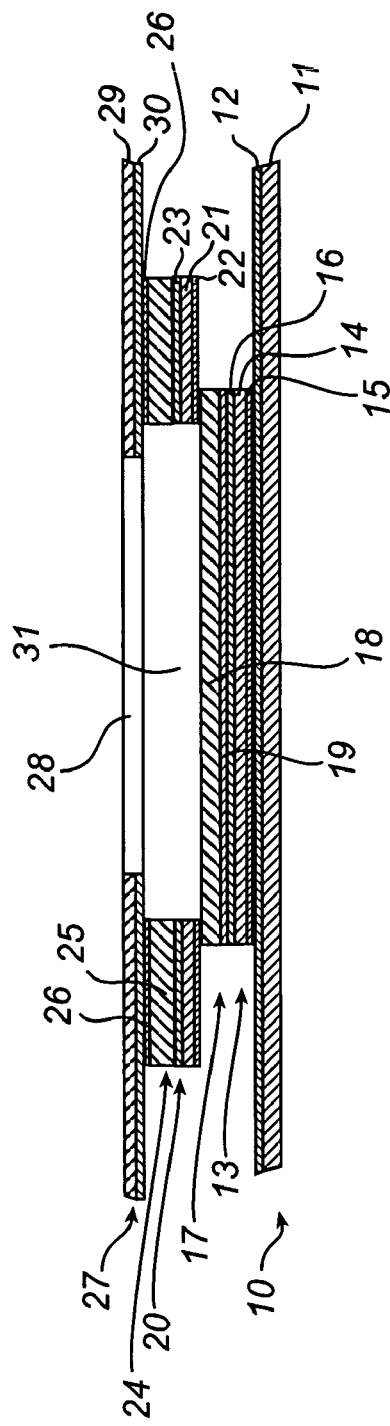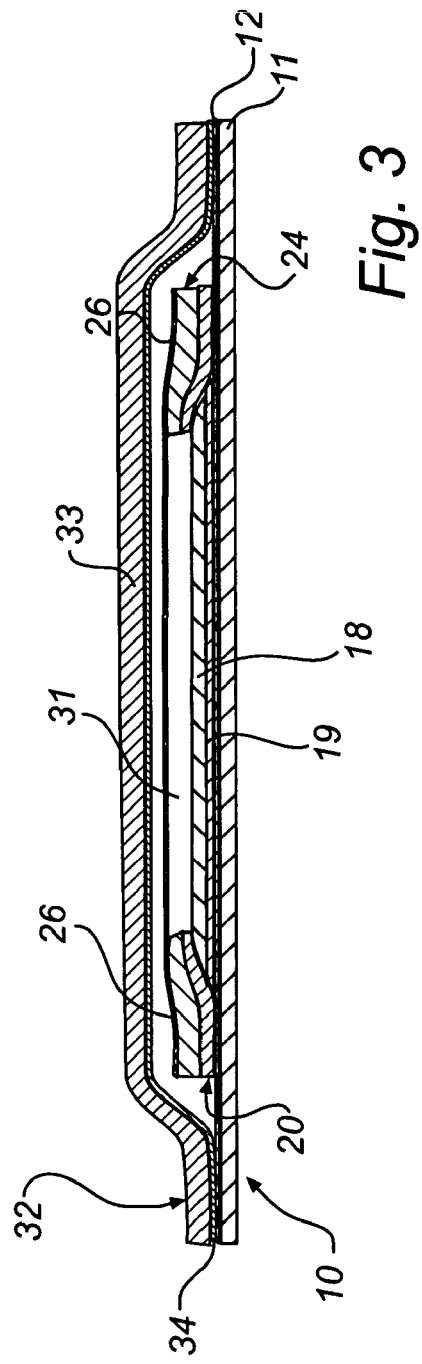

EPICUTANEOUS TEST PLASTER

BACKGROUND

When testing patients for allergy, an epicutaneous test plaster is commonly used, which has a number of test chambers which in connection with use of the test plaster can be loaded with various allergens. The test chambers contain a filter paper for application or absorption of the allergens and are arranged at a suitable distance from each other to make it possible to separately assess the effect of the various allergens.

A prior-art epicutaneous test plaster, which is widely used, is made up of a flexible carrier with an adhesive layer for removable adhesion of the epicutaneous test plaster to the skin of the tested patient. The carrier is essentially made of a medical tape with a hypoallergen adhesive layer. The test chambers of this prior-art test plaster are formed as shallow square plastic cups with an outwardly directed flange. The test chambers are then fixed, spaced from each other, to the carrier of the epicutaneous test plaster and are distributed over the surface of the carrier in a suitable pattern. In the test chambers, a filter paper can be inserted to serve as an absorbent for allergen substances which are later to be inserted into the test chambers. A cover layer is applied over the test chambers and kept in place on the carrier by means of the adhesive layer of the carrier.

In a prior-art embodiment, the cover layer has the form of a blister sheet which is made of a suitable plastic material and has low blister rises with the same distribution and location as the test chambers. The blister rises have a larger inner width than the test chambers and extend down round the test chambers when the cover layer is applied to the epicutaneous test plaster and is kept in place by means of the adhesive layer of the carrier. By the cover layer being kept in place on the carrier by means of the adhesive layer of the carrier, the medical staff can remove the cover layer, load the test plaster with adequate allergens and then either directly perform the test of the patient or reseal the test plaster until it is to be used on a later occasion.

This known test plaster with a blister cover layer has great advantages owing to its composition and resealability and also the rigidity which is imparted to the test plaster by the cover layer and which facilitates handling. However, manufacture of this test plaster is associated with certain difficulties, inter alia, since the cup-shaped test chambers must be made separately and subsequently, in connection with mounting on the carrier, be oriented in the correct way and then secured to the carrier, and since it is difficult to attach the requisite filter paper in the test chambers without the use of adhesive for this purpose. Therefore the filter paper is applied manually on the actual patient testing occasion when using the known test plaster.

NL-8701577-A discloses and describes an allergy testing device which comprises a carrier with an adhesive layer for holding a flexible strip, which is made of a cellular plastic material with closed cells and which has punched-out portions to form test chambers. A moisture-proof layer and an absorbing layer are inserted in the test chambers to enable holding of the allergen material that is to be used in the testing for allergy. When using the testing device according to FIG. 1 of NL-8701577-A, the testing device is applied to the patient's skin by means of a suitable surgical tape while the carrier with its adhesive layer in the embodiments according to FIGS. 2-4 is extended past the long side edges of the flexible strip so as to be directly applied to the skin without necessitating additional tape. In all embodiments, a cover strip is used, which has its own adhesive layer to be able to be temporarily held on the underlying parts of the testing device. A serious drawback of this known testing device is that the allergen material in the test chambers can leak out from the test chambers, on the one hand through the underside of the indentations in the test chamber and, on the other hand, over the actual edge of the frame of the test chamber. When leaking down through the underside of the test chamber, the test allergen reaches the porous tape and can penetrate therethrough and contaminate the patient's clothing. When leaking over the edge of the frame, the test allergen is spread over the skin surface towards neighbouring test chambers. This is a serious drawback since the assessment of the allergy reactions is rendered difficult.

SUMMARY

An object of the present invention is to provide an epicutaneous test plaster, which has additional advantages in connection with use of the epicutaneous test plaster by limiting the spreading of the allergen material outside the test chambers when using the epicutaneous test plaster.

To achieve this and other objects of the invention, the invention starts from a known epicutaneous test plaster which has a flexible carrier with a medical adhesive layer and a number of test chambers. The test chambers contain a filter element for absorption of allergen and are oriented with their opening directed away from the flexible carrier. A removable cover layer extends over all the test chambers and the carrier and is removably secured to them by means of the adhesive layer of the carrier. According to the invention, the test chambers are formed as separate chambers which are each fixed to the carrier and are made up of a number of different sub-layers.

To satisfy the above objects, the invention thus is aimed at the designing of the test chambers and the composition thereof. Instead of premanufacturing a shallow cup-shaped test chamber, the individual test chamber is according to the invention to be made up of a number of different sub-layers which are successively applied to the adhesive layer of the carrier. For each test chamber to be formed, there is first secured to this adhesive layer a filter paper which on its side facing the bottom layer is laminated with a moisture barrier layer. This securing can, in a preferred embodiment, be achieved by means of an adhesive layer, whose one side is fixed to the moisture barrier layer of the filter paper and whose other side is fixed to the adhesive layer of the carrier. Alternatively, this adhesive layer can be made of a flexible double-adhesive tape which forms a bottom layer. Subsequently, a frame-shaped foam plastic layer is secured, which forms the side walls of the test chambers and which on its outwardly directed upper side has a layer of medical adhesive. The securing of this frame-shaped foam plastic layer can take place either by making the foam plastic layer as a double-adhesive tape or by using a separate adhesive layer, whose one side is fixed to the foam plastic layer and whose other side is fixed to the filter element, or by arranging a frame-shaped fixing layer made of a flexible double-adhesive tape between the foam plastic layer and the filter element.

In the final applying of the cover layer, it is fixed to the rest of the epicutaneous test plaster by means of the adhesive layer of the carrier and, in the case where the cover layer consists of a silicone-treated paper liner, also by means of the outwardly directed adhesive layer of the frame-shaped foam plastic layer. The cover layer may consist of an ordinary release paper backing (liner) which advantageously has openings opposite to the test chambers, so that the medical staff can load the test plaster just before use when the cover layer is pulled off to expose the adhesive layers and in connection with the application to the patient's skin.

However, the cover layer is preferably formed as a blister sheet with blister rises or bubbles, which have a greater width than the individual test chambers and which, when the blister sheet is applied to the test plaster, enclose them, the blister sheet being kept in place on the rest of the epicutaneous test plaster by means of the adhesive layer of the carrier round each individual test chamber. In a particularly preferred embodiment of the blister sheet, the blister rises are provided with a central portion which is so strongly bent down towards the carrier that it is in contact with the corresponding frame-shaped foam plastic layer's layer of medical adhesive to seal the corresponding test chamber.

By making the test chambers of different layers of a soft flexible material, further advantages are achieved by the epicutaneous test plaster, when used, better conforming to the shape and contour of the skin portion to which it is fixed. This combined with the circumstance that the frame-shaped foam plastic layer has an outwardly directed adhesive layer minimises, or fully eliminates, the risk that allergens will spread to the area outside each individual test chamber. In the known test chambers consisting of premanufactured shallow plastic cups, it has been found that the rigidity of the test chambers sometimes has resulted in gaps arising between the patient's skin and the test chambers. In the testing devices according to the above-mentioned NL-8701577-A, the strip-shaped element forming the test chambers abuts freely against the patient's skin, and therefore there is no seal in any direction, which makes the risk of gaps and the risk of spreading very great.

According to the present invention, compared with prior-art represented by NL-8701577-A, it is possible to avoid that the tested skin portion is irritated and turns red, which disturbs the test reading and makes it difficult. In the test plaster according to the invention, the surface portion of the test plaster which abuts against the skin is therefore minimised by the outer edges of the test chambers being made narrow and frame-shaped. This important aspect has not been taken into consideration in the above NL-8701577-A, since the test chambers actually do not consist of a test chamber with a narrow enclosing non-porous frame, but instead consist of a part, large in surface area, of a non-porous cellular plastic material with punched-out small test chambers. As a result, the skin cannot breathe on large parts of the testing device. The reason for using a porous, moisture- and air-permeable carrier of surgical tape is that, to avoid skin irritation, the skin must be able to breathe and let through moisture which is naturally present on the skin and which is generated in excess when sweating.

A further great advantage of the invention is obtained by the use of a stronger adhesive in the adhesive layers that are used to secure the test chambers to the carrier and to connect the different sub-layers of the test chambers with each other. This condition eliminates the risk that the test chambers or parts of them should come loose from the carrier when the cover layer is removed in connection with use of the epicutaneous test plaster.

BRIEF DESCRIPTION OF THE DRAWINGS

Three particularly preferred embodiments of the invention will now be described with reference to the accompanying drawings, in which FIG. 2 is a very schematic section through a test chamber when applied to the carrier of the test plaster and provided with a cover layer, the various parts of the test chamber being, for the sake of clarity, not completely joined and also not shown to scale, FIG. 3 shows a second embodiment in which a blister sheet is used as cover layer.

Figure 1:
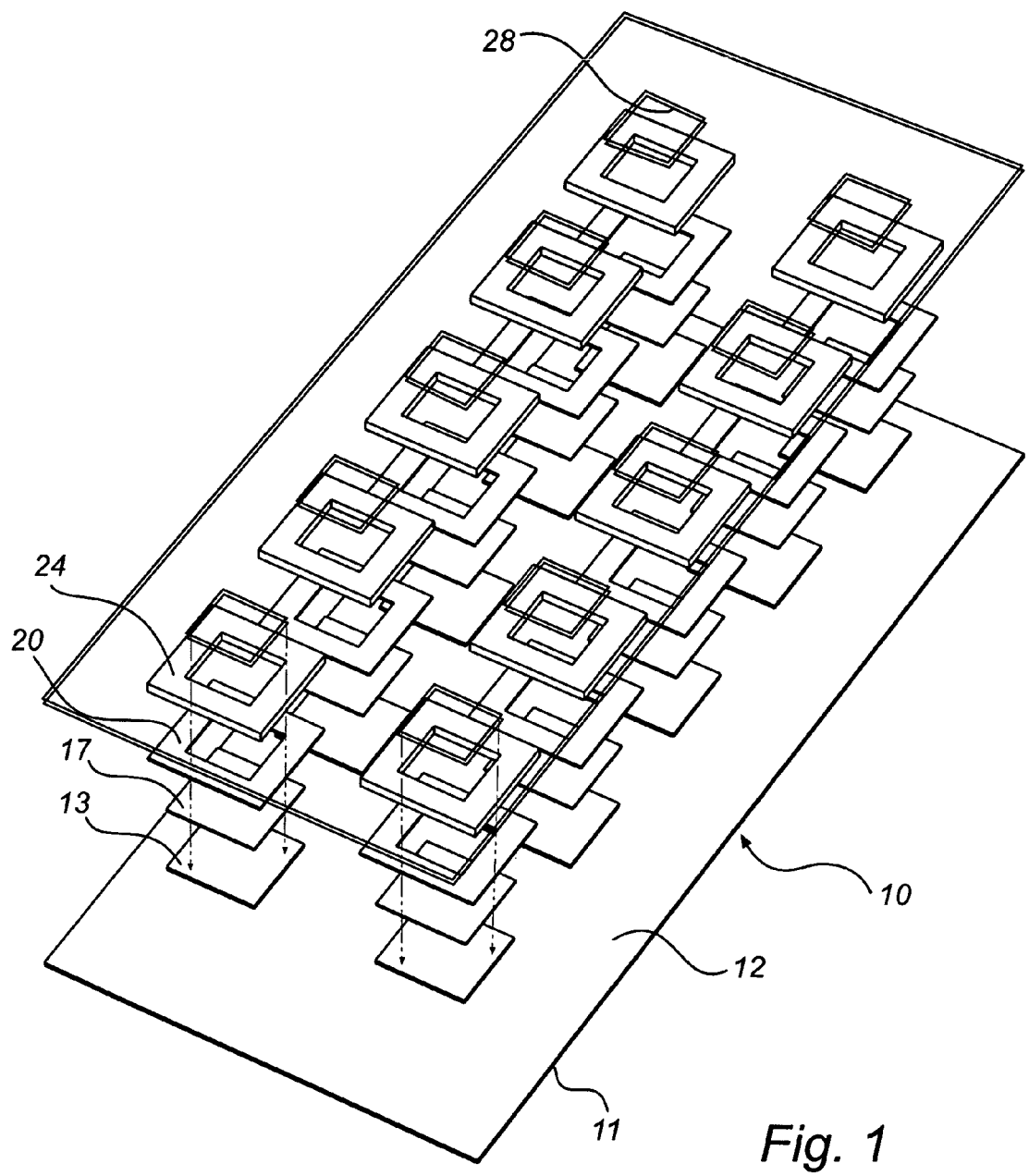
FIG. 1 is an exploded view of a first embodiment with the different sub-layers spaced from each other.

The exploded view in FIG. 1 shows how the different layers in a preferred embodiment of an epicutaneous test plaster according to the invention are arranged. At the bottom there is a carrier 10 which consists of a tape web 11 with an adhesive layer 12 which in the drawing is directed upwards. In a particularly preferred embodiment, a medical tape number No. 1529 (Film-nonwoven Composite Medical Tape) purchased from 3M is used as carrier. The non-woven layer of this medical tape is made of rayon and is coated with a hypoallergen pressure-sensitive acrylate adhesive. However, other carriers with equivalent properties can also be used. An example of such an alternative carrier is a medical tape 9907 T/W marketed by 3M. In this tape, the non-woven layer consists of a multilayer of polyurethane rubber, which is elastic and possesses an extremely high air permeability and which is coated with an hypoallergen pressure-sensitive acrylate adhesive. The elasticity and the water-resistant polyurethane material result in a unique property implying that the tested patients are not restricted by activities such as hard physical work, gymnastics and sports as well as showering, bathing and swimming. These restrictions appear in testing with test plasters known up to now, and there is a great risk of the test plaster falling off or being damaged when subjected to the above loads.

According to the invention, the actual test chambers 31 are made up of different sub-layers. At the bottom there is a bottom layer 13 in the form of a double-adhesive tape. The bottom layer has the same extent as, or a slightly greater extent than, the test chamber to be formed, and a number of bottom layers are fixed to the medical adhesive layer 12 of the carrier 10, suitably distributed and suitably spaced from each other. A common size of such epicutaneous test plasters has ten essentially square test chambers about 10×10 mm, arranged in two juxtaposed rows with a mutual distance of about 10 mm between the individual test chambers and between the two rows.

In a currently preferred embodiment of the epicutaneous test plaster according to the invention, use is made of a double-adhesive transparent polyester tape to form the bottom layer 13, the tape web 14 of the tape having adhesive layers 15, 16 which are preferably formed of a rubber-based adhesive. A particularly preferred double-adhesive tape can be obtained from Avery Dennison Corporation, Specialty Tape Division, Belgium under the designation Med 2134 Wetstick™.

Thus the bottom layer 13 is strongly secured to the carrier 10 and to a filter element 17 which has essentially the same extent as the bottom layer. The filter element is made up of a filter layer 18, which on its side facing the bottom layer is laminated with a liquid impermeable cover layer 19, preferably of polyethylene. The filter layer is preferably cellulose-based and has high liquid absorbency. The same type of filter unit as used in prior-art epicutaneous test plasters can advantageously be used.

A frame-shaped fixing layer 20 of double-adhesive tape is applied to the outside of the filter element 17. This fixing layer can suitably be made of the same type of double-adhesive tape as the bottom layer 13 and has a tape web 21 with the adhesive layers 22, 23.

In a particularly preferred embodiment, the frame-shaped fixing layer 20 has such a shape as to cover a rim portion of the filter element 17 and extend outside this to be able to adhere to the adhesive layer 12 of the carrier 10 and, thus, fix the fixing layer more firmly to the carrier than would this adhesive layer do in the normal case. If the filter element 17 is square 12×12 mm, the frame-shaped fixing layer 20 can have an inner free square opening 10×10 mm. Also other dimensions are possible.

The frame-shaped fixing layer 20 is used to secure another frame-shaped element 24 which is to form the side walls of the test chamber 31 and which consists of a liquid-impermeable foam plastic material 25. Since this frame-shaped element of foam plastic material is to be sealed against the skin to which the epicutaneous test plaster is applied, the free upper side of this frame-shaped element is provided with an adhesive layer 26 of a medical type. The thickness of this frame-shaped element determines the depth of the test chamber 31. About 1 mm has been found to be a suitable thickness. A particularly preferred material to form this layer can be obtained from Avery Dennison Corporation, Specialty Tape Division, Belgium under the designation Med 5666R Wet-stick™. This material is a single-coated polyethylene foam layer with a thickness of about 1 mm and with a medical adhesive layer 26 on its side directed outwards.

The finishing layer is a cover layer 27. The cover layer may consist of a normal paper liner 29 with a release layer 30 on its side lacing the adhesive layers 12 and 26. The cover layer has in this case advantageously openings 28 opposite to the test chambers, so that the medical staff just before use can load the test plaster with the allergen materials which are to be tested on the patient.

The embodiment shown in FIG. 3 is the currently most preferred and has a cover layer 32 in the form of a blister sheet 32 with blister rises 33. The main layer of the blister sheet can consist of PVC, and this main layer can advantageously be laminated with a polyethylene layer 34 which has lower adhesive force against the adhesive layer 12 of the carrier 10 than does a layer of PVC.

The blister rises of the blister sheet have a larger inner width than the test chambers 31 to allow the blister bubbles of the blister sheet, when the blister sheet is applied to the test plaster, to enclose the test chambers and to allow the blister sheet to abut against and be held by the adhesive layer 12 of the carrier 10 round each individual test chamber. In this embodiment, the blister bubbles are so deep that there is no contact between the blister sheet and the adhesive layer 26 of the frame-shaped foam plastic layer 24 when the blister sheet is mounted.

Figure 5:
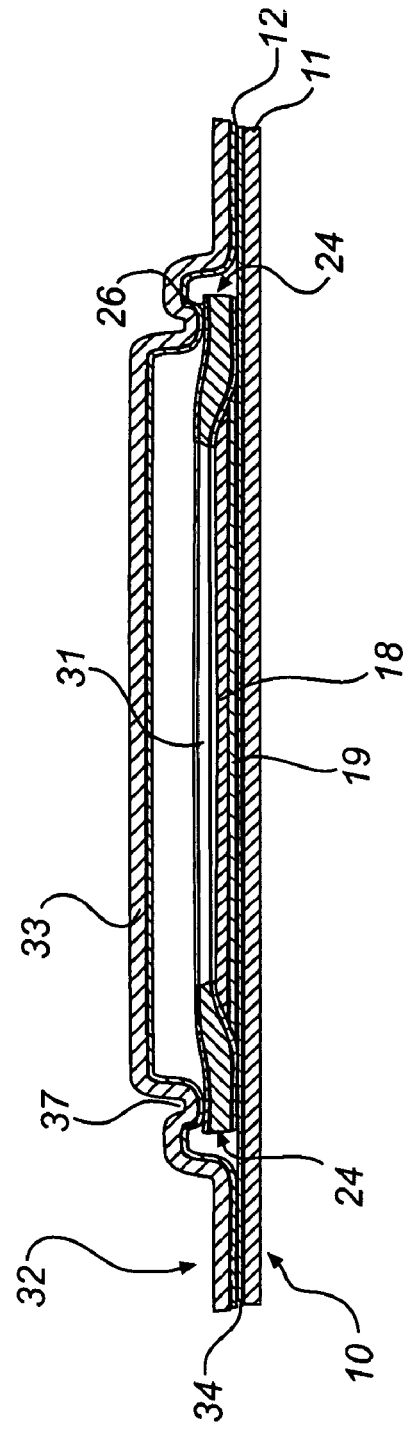
FIG. 5 shows an alternative to the embodiment according to FIG. 3.

FIG. 5 illustrates, however, a different embodiment of the blister sheet 32 which in this case is formed with a circumferential groove 37 which extends down towards the frame-shaped foam plastic layer 24 and its adhesive layer 26 to form a cover over the test chamber 31 and seal it. This embodiment of the invention is particularly advantageous in the cases where the medical staff wants to load the epicutaneous test plasters with allergens in advance and then store the loaded test plasters until the different patients are to be tested. By sealing each test chamber, the risk of contamination and leakage between neighbouring test chambers is reduced when handling the loaded test plasters.

Figure 4:
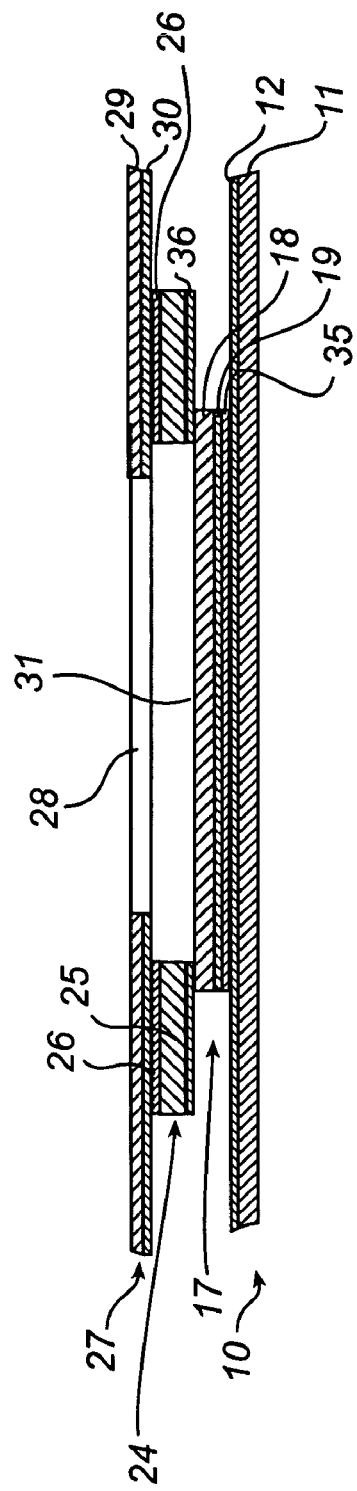
FIG. 4 shows an alternative to the embodiment according to FIG. 2.

FIG. 4 illustrates an additional embodiment of the test plaster according to the present invention. This preferred embodiment is based on the same principle as the embodiments according to FIGS. 1-3 by the individual test chambers being formed by successive application of a number of different sub-layers.

The embodiment according to FIG. 4 differs from the embodiments according to FIGS. 1-3 in two respects. First, the bottom layer 13 of double-adhesive tape is replaced by an individual adhesive layer 35, whose one side is fixed to the medical adhesive layer 12 and whose other side is fixed to the liquid impermeable cover layer 19 of the filter element 17. Such double-adhesive layers can be obtained from MacTac, USA under the designation MacFilm F2023.

In the embodiment according to FIG. 4, the fixing layer 20 has been left out, and the frame-shaped foam plastic layer 24, which forms the test chambers 31, is formed as a double-adhesive tape, i.e. the foam plastic layer 24 has an adhesive layer on both sides, i.e. the layer 26 and the layer 36. Such a double-adhesive tape with a carrier of foam plastic can be obtained from Scapa Tapes, USA, under the designation RX432 VSA. The foam plastic layer of this tape consists of a polyethylene foam layer, and the two adhesive layers consist of a hypoallergen pressure-sensitive acrylate adhesive.

The use of a blister sheet makes the handling of the test plasters easier since they will be more rigid. This embodiment also has the advantage that it is suited for preloading of the test plasters with allergen before use of the test plasters and can therefore be used for premanufacture of test plasters ready for use. In this case, the blister layer is temporarily removed while loading takes place, after which it is again applied to seal the area round each individual test chamber. Storing of the loaded plasters can then take place in a manner which is convenient from the clinical point of view.

In the shown embodiment, the test chambers are made square since this makes it easier to distinguish between real allergic reactions and common skin irritation. However, other shapes are feasible, such as circles, ellipses, rectangles or polygons. The different sub-layers can be made of other materials than those mentioned above as long as use is made of a medical adhesive for the adhesive layer portions which are to be in contact with the patient's skin during testing for allergy.

The invention claimed is:

1. An epicutaneous test plaster, comprising:
    a flexible carrier including an adhesive layer for removable adhesion of the epicutaneous test plaster to a skin portion;
    a plurality of test chambers distributed over the adhesive layer of the carrier; and
    a removable cover layer extending over all the test chambers and the carrier,
    wherein the test chambers are formed as separate chambers, each test chamber including,
        a support element secured to the carrier and including a support layer adhered to a moisture barrier layer,
        a frame-shaped foam plastic layer secured on top of and embracing the support element, the frame-shaped foam plastic layer having an outwardly directed side on which is provided a first layer of adhesive, the frame-shaped foam plastic layer defining at least some sidewalls of the test chamber that directly confront each other, and
        a second layer of adhesive interposed between the frame-shaped foam plastic layer and the support element, and
    wherein the cover layer is removably secured by way of the adhesive layer of the carrier.

2. An epicutaneous test plaster as claimed in claim 1, wherein the cover layer is a plastic layer with blister bubbles, which have the same distribution and location as the test chambers, and which are larger than the test chambers to enclose the test chambers.

3. An epicutaneous test plaster as claimed in claim 2, wherein the cover layer consists of a plastic layer laminate with a polyethylene layer that faces the test chambers.

4. An epicutaneous test plaster as claimed in claim 2, wherein each of the blister bubbles of the cover layer has a groove in contact with the first layer of adhesive of a corresponding frame-shaped foam plastic layer.

5. An epicutaneous test plaster as claimed in claim 1, wherein the cover layer consists of a paper liner with a silicone layer that faces the test chambers.

6. An epicutaneous test plaster as claimed in claim 1, wherein the carrier consists of a flexible porous surgical tape with a methacrylate-based adhesive layer.

7. An epicutaneous test plaster as claimed in claim 1, wherein the support layer of the support element is cellulose-based.

8. An epicutaneous test plaster as claimed in claim 1, wherein the frame-shaped foam plastic layer consists of a polyethylene foam.

9. An epicutaneous test plaster as claimed in claim 1, wherein the support element is secured to the carrier by way of a bottom layer of a flexible double-adhesive tape.

10. An epicutaneous test plaster as claimed in claim 9, wherein the double-adhesive tape which forms the bottom layer has adhesive layers of a synthetic rubber-based adhesive.

11. An epicutaneous test plaster as claimed in claim 1, wherein the support element is secured to the carrier by way of an adhesive layer, whose one side is fixed to the carrier and whose other side is fixed to the support element.

12. An epicutaneous test plaster as claimed in claim 1, wherein the frame-shaped foam plastic layer is secured to the support element by way of a frame-shaped fixing layer of a flexible double-adhesive tape, arranged on top of the support element and surrounds the same.

13. An epicutaneous test plaster as claimed in claim 12, wherein the frame-shaped fixing layer of flexible double-adhesive tape partially covers a rim portion of the support element and extends outside said rim portion.

14. An epicutaneous test plaster as claimed in claim 13, wherein the frame-shaped fixing layer of flexible double-adhesive tape has adhesive layers made of a synthetic rubber-based adhesive.

15. An epicutaneous test plaster as claimed in claim 1, wherein the frame-shaped foam plastic layer is formed as a double-adhesive tape.

16. An epicutaneous test plaster as claimed in claim 3, wherein each of the blister bubbles of the cover layer has a groove in contact with the layer of adhesive of a corresponding frame-shaped foam plastic layer.

17. An epicutaneous test plaster, comprising:
a carrier including an adhesive layer; and
a plurality of test chambers distributed over the adhesive layer of the carrier, each test chamber including,
a support element mounted on the carrier,
a frame-shaped foam plastic layer having a lower surface mounted on the support element, and an upper surface with adhesive means for attaching the frame-shaped foam plastic layer to a test area, the frame-shaped foam plastic layer defining at least some sidewalls of the test chamber that directly confront each other, and
a layer of adhesive interposed between the frame-shaped foam plastic layer and the support element;
wherein the foam plastic layers of the test chambers are spaced apart from each other.

18. An epicutaneous test plaster as claimed in claim 17, wherein the adhesive means is an adhesive layer that extends all the way around the perimeter of an interior of a corresponding test chamber.

19. An epicutaneous test plaster, comprising:
a carrier including an adhesive layer;
a plurality of test chambers distributed over the adhesive layer of the carrier, each test chamber including,
a support element mounted on the carrier, and
a frame-shaped foam plastic layer mounted on the support element, the frame-shaped foam plastic layer defining at least some sidewalls of the test chamber that directly confront each other;
a first adhesive layer provided on an outwardly directed side of the frame-shaped foam plastic layer, the adhesive layer including an opening through which an interior of the test chamber is exposed; and
a second adhesive layer interposed between the frame-shaped foam plastic layer and the support element.

20. An epicutaneous test plaster as claimed in claim 19, further comprising a cover layer which is a plastic layer with blister bubbles, which have the same distribution and location as the test chambers.

* * * * *